United States Patent [19]
Coates

[11] Patent Number: 5,911,696
[45] Date of Patent: Jun. 15, 1999

[54] INTEGRAL STRAP HANDLING DEVICE FOR A LEG CAST

[76] Inventor: Irvin Coates, 341 Mount Oriole La., Linden, Va. 22642

[21] Appl. No.: 08/803,023

[22] Filed: Feb. 19, 1997

[51] Int. Cl.[6] ................................. A61F 5/00; A61F 5/37
[52] U.S. Cl. ............................................... 602/4; 128/882
[58] Field of Search .............................. 602/3–6, 23, 27, 602/60–62; 128/882, DIG. 15; 606/201, 203; 224/267, 268, 254; 119/770, 792, 793, 795, 797; D30/152, 153

[56] References Cited

U.S. PATENT DOCUMENTS

| | | |
|---|---|---|
| 1,490,381 | 4/1924 | Gobar . |
| 2,460,589 | 2/1949 | Lewis . |
| 2,543,847 | 3/1951 | Hallstedt . |
| 2,607,340 | 8/1952 | Anderson . |
| 3,739,772 | 6/1973 | Ennis . |
| 3,797,483 | 3/1974 | Feldman ...................... 128/DIG. 15 X |
| 4,019,503 | 4/1977 | Smith . |
| 4,252,112 | 2/1981 | Joyce . |
| 4,294,238 | 10/1981 | Woodford . |
| 4,355,635 | 10/1982 | Bihl et al. .................... 128/DIG. 15 X |
| 4,461,288 | 7/1984 | Curtis .......................................... 602/23 |
| 4,854,313 | 8/1989 | Kloepper . |
| 5,014,692 | 5/1991 | Rhoades .................................... 602/23 |
| 5,256,119 | 10/1993 | Tudor . |
| 5,360,019 | 11/1994 | Witzel et al. ............... 128/DIG. 15 X |

Primary Examiner—Linda C. M. Dvorak
Assistant Examiner—Denise Pothier
Attorney, Agent, or Firm—Jones, Volentine, Steinberg & Whitt, LLP

[57] ABSTRACT

An integral strap handling device for a casted foot includes an instep strap extending from one side of the ankle to the other over a casted foot, a heel strap extending from one side of the ankle to the other around the heel, and a sole strap extending from one side of the ankle to the other under a casted foot. The instep, heel, and sole straps are connected to each other via rings to allow movement of the straps so as to provide a secure fit for the integral strap when placed over cast. Another connector attaches an assist strap to the instep strap to provide for increased mobility of the casted foot.

15 Claims, 3 Drawing Sheets

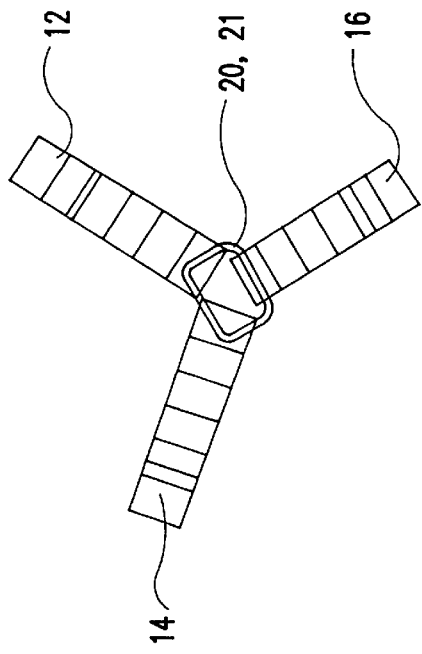
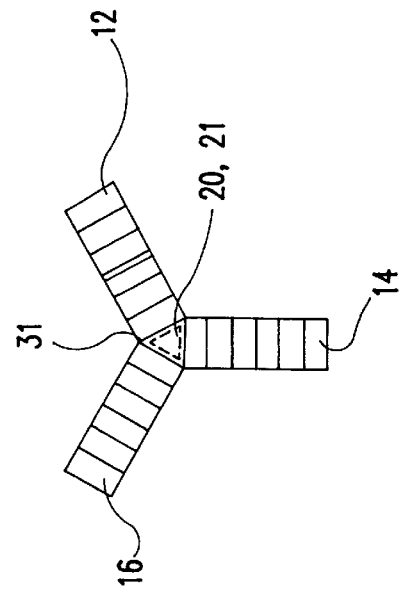
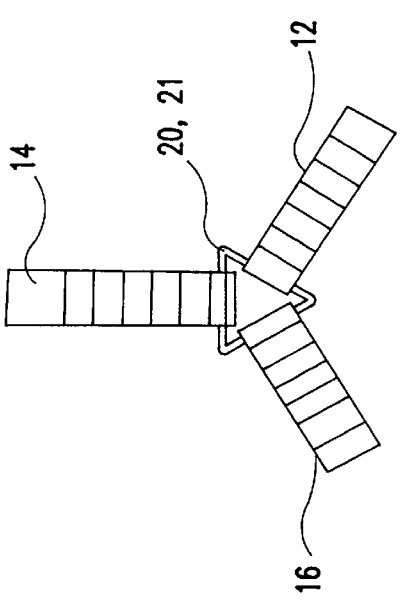
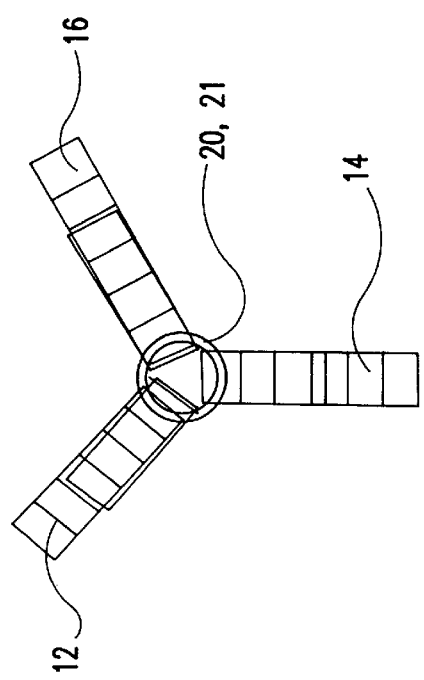

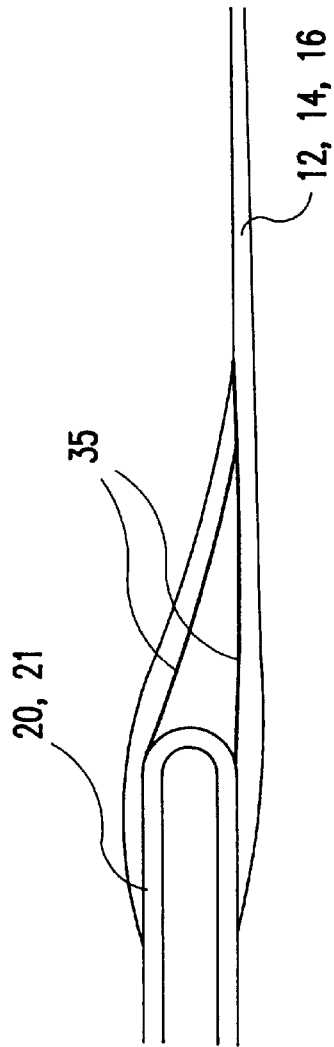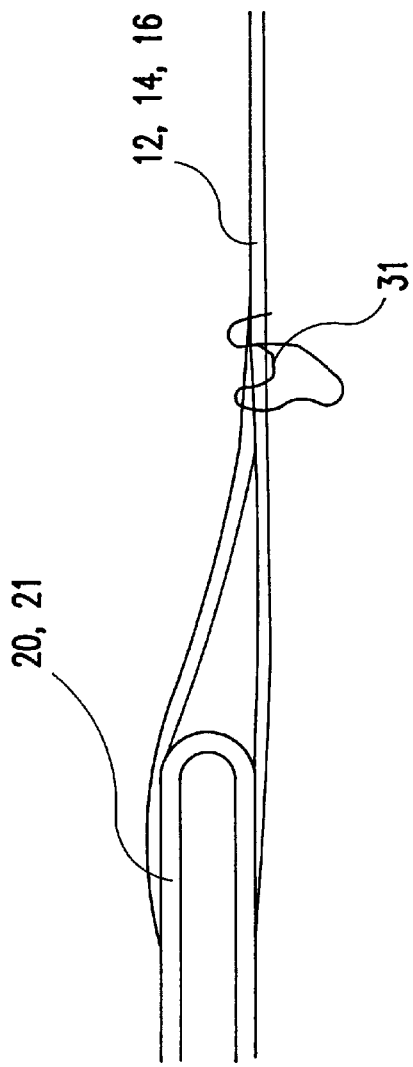

5,911,696

INTEGRAL STRAP HANDLING DEVICE FOR A LEG CAST

BACKGROUND OF THE INVENTION

1. Field of the Invention

The present invention generally relates to a strap handling device for a leg cast, and more particularly, to a foot and ankle strap having an integrated strapping system that provides for a secure, customized fit regardless of the cast size, as well as providing for ease of application and removal of the integrated strapping handling device.

2. Description of the Related Art

Hard, rigid casts are used on a variety of injuries affecting the legs between the ankle and the hip. Such injuries include, for example, a broken or damaged femur, tibia, fibula, or patella. Surgery on leg or knee bones and associated cartilage may also require the use of a cast to immobilize the affected area during the healing process.

Generally, the affected area is placed in a plaster cast. Although such casts are very effective in healing broken or fractured limbs, they do have several disadvantages. Depending on the location and nature of the injury, such casts frequently have to cover a major portion of the leg. In particular, when the cast covers the knee and a major portion of the upper leg, the patient experiences great difficulty in moving the casted leg. This is due to the weight of the cast itself combined with the inability to use the muscles affected by the immobilizing cast.

As a result, simple movements such as getting in and out of bed, sitting or getting off a chair, walking up and down stairs, entering and exiting a car, and other routine tasks require sustained effort and additional time to accomplish. In severe cases, the patient may not be able to move about without the help of an attendant.

Various devices have been proposed to alleviate this longstanding problem. Such devices are disclosed in, for example, U.S. Pat. Nos. 2,607,340 to Anderson; 3,739,772 to Ennis; 4,019,503 to Smith; 4,252,112 to Joyce; 4,294,238 to Woodford; 4,854,313 to Kloepper; and 5,256,119 to Tudor. The devices, however, have several disadvantages. Some are complicated arrays of straps, buckles and bars, designed for use in a hospital or with the aid of an attendant. Others are not capable of providing a secure fit and may easily slip off during movement of the leg, perhaps resulting in great discomfort or pain as the raised limb hits the floor.

A need exists, therefore, for a strapping system that aids a patient in achieving individual mobility, while providing a secure, customized fit regardless of the size of the cast. The strapping system should also be designed for easy attachment and removal.

SUMMARY OF THE INVENTION

Accordingly, the present invention is directed to an integral strap handling device for a cast which substantially overcomes one or more limitations of the prior art. The invention provides several features which greatly enhance the fit of the foot and ankle strap, as well as being characterized by the ease of applying and removing the strap from the cast.

To achieve these and other advantages and in accordance with the purpose of the invention, as embodied and broadly described, the invention is an integrated strap handling device for a casted foot, comprising: an instep strap connected at one end to a first connecting means and at the other to a second connecting means, the instep strap extending over the instep area of the casted foot; a sole strap connected at one end to the first connecting means and at the other to the second connecting means, the sole strap extending under the sole area of the casted foot; a heel strap connected at one end to the first connecting means and at the other to the second connecting means, the heel strap extending around the upper heel area of the casted foot; and a third connecting means for connecting the instep strap to one end of an assist strap.

BRIEF DESCRIPTION OF THE DRAWINGS

The foregoing and other objects, aspects, and advantages will be better understood from the following detailed description of the embodiments of the invention with reference to the drawings, in which:

FIGS. 2A–2D are side views of the various connections for the first and second connecting means of the present invention; and FIGS. 3A and 3B are side views of two connection methods for the strap of the present invention.

DETAILED DESCRIPTION OF THE INVENTION

Figure 1:
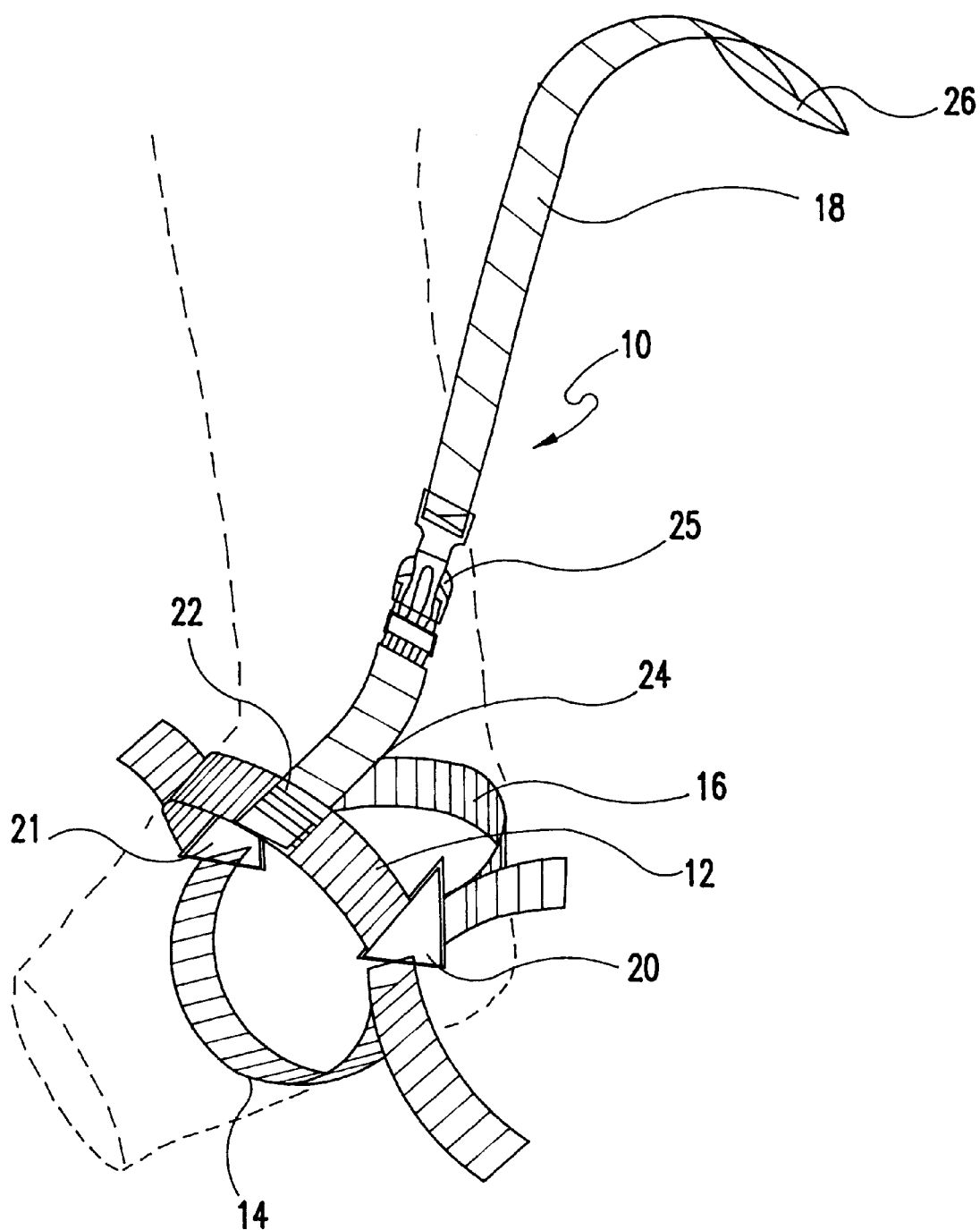
FIG. 1 is a perspective view of the ankle strap of the present invention as it appears wrapped around a casted foot (shown as the dotted lines)

The invention is directed to an integrated strap handling device for a casted foot that provides for a secure, customized fit regardless of the cast size, as well as ease of applying and removing the ankle strap. The invention may be utilized for both below-the-knee and above-the-knee casts, although it is especially useful for above-the-knee casts where reduced limb maneuverability is a problem.

Reference will first be made FIG. 1, which illustrates an embodiment of the integrated strap handling device of the present invention. The integrated strap handling device 10 is comprised of an instep strap 12, a sole strap 14, and a heel strap 16. The straps may be made of any suitable strap material, for example, leather, nylon, or the like. As shown in FIG. 1, the instep strap 12, sole strap 14, and heel strap 16 are connected at one end to a first connecting means 20 and at the other to a second connecting means 21.

More specifically, the instep strap 12 extends from the first connecting means 20 on one side of the patient's ankle to the second connecting means 21 on the other side of the ankle over the instep area of the casted foot. The sole strap 14 extends from the first connecting means 20 on one side of the patient's ankle to the second connecting means 21 on the other side ankle under the sole area of the casted foot. Heel strap 16 extends from the first connecting means 20 on one side of the ankle to the second connecting means 21 on the other side of the ankle around the upper heel area of a casted foot.

The first and second connecting means 20, 21 are meant to provide for some movement of the respective instep 12, sole 14, and heel 16 straps to accommodate different size casts to ensure a secure, custom fit.

The first and second connecting means 20, 21 may take on several forms as shown in FIGS. 2A–2D. In FIG. 2A. the first and second connecting means are triangular rings. In FIG. 2B, the first and second connecting means are D-shaped rings. In FIG. 2C, the first and second connecting means are annular rings. As stated above, each of these connecting means allow movement of the respective instep, sole, and heel straps to accommodate different size casts. Although not preferred, FIG. 2D illustrates a connecting means composed merely of the instep strap 12, sole strap 14, and heel strap 16 being connected to each other by threads 31 or other equivalent securing means.

FIGS. 3A and 3B illustrate two methods of connecting the instep 12, sole 14, and heel 16 straps to the first and second connecting means. As shown in FIG. 3A, each of the straps 12, 14, and 16 may contain a hook and loop fastener portion 35 such as VELCRO that may be looped around the connecting means 20, 21 and then folded back upon itself to secure the strap. The hook and loop fastener portion 35 35 is similar to that typically seen in the prior art. The use of the hook and loop fastener portion 35 is advantageous in that the respective straps may be fitted to conform to the casted foot.

An alternate embodiment is illustrated in FIG. 3B. Rather than using a hook and loop fastener the straps are connected via conventional threads 31 or other equivalent means. Such an embodiment, however, does not allow each of the straps to be custom fitted by the user.

Referring again to FIG. 1, a third connecting means 24 connects the instep strap 12 to one end of an assist strap 18. In this embodiment, the third connecting means comprises a male-end snap-buckle 25 attached at one end and a loop portion 22, which wraps around the instep strap 12, at the other end. The assist strap 18 is fitted with the female end of the snap-buckle 25. The snap-buckle 25 provides for ease of use as well as strength for lifting and otherwise moving the casted limb. The assist strap 18 may be easily removed, when sleeping for example, by disengaging the snap-buckle 25.

The assist strap 18 includes a hook and loop fastener portion 26, such as VELCRO, at the non-attached end to allow the patient to manipulate the assist strap 18, as well as allow the assist strap 18 to be affixed to the belt, belt loop, or other attachment point on the patient when not in use.

To put the integrated strap handling device on, the patient need only temporarily unhook one end of the instep 12, sole 14, or heel strap 16, from either the first 20 or second 21 connecting means, then slide the casted foot into the strap handling device, and then reattach the respective strap to the respective connecting means. Of course, two or more straps may be unhooked and reattached at the discretion of the patient.

It is understood that many modifications are contemplated within the practice of the present invention. Specifically, any of the connecting means in FIGS. 2A–2D may be combined with any of the connecting methods in FIGS. 3A and 3B. Also, any two of the three straps may be combined into a single strap, although such a method reduces the customized nature of the integrated strap handling device. In addition, different embodiments of the connecting means in FIGS. 2A–2D may be used within a single strap handling device.

It will be apparent to those skilled in the art that various modifications and variations can be made in the system and method of the present invention without departing from the spirit or scope of the invention. Thus, it is intended that the present invention cover the modifications and variations of this invention provided they come within the scope of the appended claims and their equivalents.

Having thus described my invention, what I claim as new and desire to secure by Letters Patent is as follows:

1. An integrated strap handling device for a casted foot, comprising:
an instep strap connected at one end to a first connecting means and at the other end to a second connecting means, the instep strap configured to extend over an instep area of the casted foot;
a sole strap connected at one end to the first connecting means and at the other end to the second connecting means, the sole strap configured to extend under a sole area of the casted foot;
a heel strap connected at one end to the first connecting means and at the other end to the second connecting means, the heel strap configured to extend around an upper heel area of the casted foot; and
an assist strap connected to the instep strap by a third connecting means.

2. The strap of claim 1, wherein said first and second connecting means are triangular rings and said instep, sole, and heel straps are connected to said triangular rings by strap loops secured by threads.

3. The strap of claim 1, wherein said first and second connecting means are D-shaped rings and said instep, sole, and heel straps are connected to said D-shaped rings by strap loops secured by threads.

4. The strap of claim 1, wherein said first and second connecting means are annular rings and said instep, sole, and heel straps are connected to said annular rings by strap loops secured by threads.

5. The strap of claim 1, wherein said instep, sole, and heel straps are fixedly connected together.

6. The strap of claim 1, wherein said first and second connecting means are triangular rings and said instep, sole, and heel straps contain hook and loop fastener portions for looping around said triangular rings and being secured by mating the hook and loop fastener portions.

7. The strap of claim 1, wherein said first and second connecting means are D-shaped rings and said instep, sole, and heel straps contain hook and loop fastener portions for looping around said D-shaped rings and being secured by mating the hook and loop fastener portions.

8. The strap of claim 1, wherein said first and second connecting means are annular rings and said instep, sole, and heel straps contain hook and loop fastener portions for looping around said annular rings and being secured by mating the hook and loop fastener portions.

9. The strap of claim 1, wherein said first and second connecting means are selected from the group consisting of an annular ring, a D-shaped ring, and a triangular ring.

10. The strap of claim 1, wherein said third connecting means includes a loop portion at one end for looping around the instep strap, and a fastening portion at a second end for attachment to the one end of the assist strap.

11. The strap of claim 10, wherein said fastening portion is a snap-buckle.

12. The strap of claim 1, further including a loop portion utilizing a hook and loop fastener at a second end of said assist strap for connecting said assist strap to a belt or belt loop on a person.

13. The strap of claim 1, wherein said third connecting means comprises threads for connecting the instep strap to the assist strap.

14. The strap of claim 1, wherein said third connecting means is a buckle.

15. An integrated strap handling device for a casted foot, comprising:
an instep-sole strap connected at one end to a first connecting means, having a midportion and configured to extend over the instep area and under the sole area of the casted foot;
a heel strap connected at one end to the first connecting means and at the other end to the instep-sole strap at the midportion, the one end and the other end being spaced apart from each other, the heel strap configured to extend around the upper heel area of the casted foot; and
an assist strap connected to the instep-sole strap between the first connecting means and the midportion by a second connecting means.

* * * * *